United States Patent
Lin et al.

(10) Patent No.: US 10,215,628 B2
(45) Date of Patent: Feb. 26, 2019

(54) IMAGE CALIBRATING METHOD AND DEVICE OF TESTING APPARATUS FOR THIN FILM TRANSISTOR SUBSTRATE

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Zijin Lin, Beijing (CN); Haisheng Zhao, Beijing (CN); Xiaoguang Pei, Beijing (CN); Chaoyang Deng, Beijing (CN); Haitao Ma, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 404 days.

(21) Appl. No.: 14/421,581

(22) PCT Filed: Jun. 30, 2014

(86) PCT No.: PCT/CN2014/081233
§ 371 (c)(1),
(2) Date: Feb. 13, 2015

(87) PCT Pub. No.: WO2015/035820
PCT Pub. Date: Mar. 19, 2015

(65) Prior Publication Data
US 2016/0033327 A1 Feb. 4, 2016

(30) Foreign Application Priority Data

Sep. 13, 2013 (CN) .......................... 2013 1 0418622

(51) Int. Cl.
| | |
|---|---|
| *G01J 1/44* | (2006.01) |
| *G06T 5/00* | (2006.01) |
| *G01N 21/95* | (2006.01) |
| *G06T 7/30* | (2017.01) |

(52) U.S. Cl.
CPC ............ *G01J 1/44* (2013.01); *G01N 21/9501* (2013.01); *G06T 5/001* (2013.01); *G06T 7/30* (2017.01);
(Continued)

(58) Field of Classification Search
CPC ....... G01J 1/44; G01J 2001/444; G06T 5/001; G06T 7/30; G06T 2207/30148; G01N 21/9501
See application file for complete search history.

(56) References Cited

U.S. PATENT DOCUMENTS

| | | | |
|---|---|---|---|
| 2005/0116184 A1* | 6/2005 | Hasegawa | G03F 7/706 250/492.2 |
| 2011/0090502 A1* | 4/2011 | Bai | G09G 3/006 356/364 |
| 2013/0148878 A1* | 6/2013 | Lin | H01L 21/67092 382/151 |

FOREIGN PATENT DOCUMENTS

| | | |
|---|---|---|
| CN | 102937816 A | 2/2013 |
| CN | 103020915 A | 4/2013 |

OTHER PUBLICATIONS

First Chinese Office Action dated Nov. 1, 2016; Appln. No. 201310416622.1.

(Continued)

*Primary Examiner* — Stephen W Smoot
(74) *Attorney, Agent, or Firm* — Ladas & Parry LLP; Loren K. Thompson

(57) ABSTRACT

The present disclosure relates to an image calibrating method and device of a testing apparatus for thin film transistor (TFT) substrate. The method comprises following steps of: calculating an image offset value by using coordinate information of each pixel in a prescribed target image obtained by the testing apparatus for the thin film transistor (Continued)

substrate; and determining whether the offset value is smaller than a prescribed threshold value, in a case where the offset value is not smaller than the prescribed threshold value, adjusting the image by using the offset value and recalculating the offset value by using the coordinate information of each pixel in the adjusted image; in a case where the offset value is smaller than the prescribed threshold value, calibrating the image obtained by the testing apparatus for the thin film transistor substrate with the offset value as a calibrating value. The calibrating efficiency and calibrating accuracy of the testing method for the thin film transistor substrate are enhanced according to the present disclosure.

11 Claims, 3 Drawing Sheets

(52) U.S. Cl.
CPC ............... *G01J 2001/444* (2013.01); *G06T 2207/30148* (2013.01)

(56) References Cited

OTHER PUBLICATIONS

International Search Report dated Dec. 9, 2014; PCT/CN2014/081233.
Written Opinion of the International Searching Authority dated Sep. 22, 2014; PCT/CN2014/081233.
The Second Chinese Office Action dated Jul. 11, 2017; Appln. No. 201318418522.1

* cited by examiner

IMAGE CALIBRATING METHOD AND DEVICE OF TESTING APPARATUS FOR THIN FILM TRANSISTOR SUBSTRATE

FIELD

The present disclosure relates to an image calibrating method and device of a testing apparatus for a thin film transistor (TFT) substrate.

BACKGROUND

In a testing process of a TFT substrate, a testing apparatus including a testing modulator and a charge-coupled device (CCD) is used to perform the test at a position of 15-20 microns above the substrate. It is necessary to align the center positions of test modulator and the CCD of the testing apparatus in order to ensure a correct testing result of the TFT substrate. Otherwise, if there is an offset between the center positions of the CCD and the modulator, testing result of the TFT substrate will have error. Therefore, it is necessary to calibrate the testing apparatus of the TFT substrate before testing the TFT substrate.

SUMMARY OF THE INVENTION

The present disclosure provides an image calibrating method and device of testing apparatus for thin film transistor (TFT) substrate. The calibrating efficiency and the calibrating accuracy of the testing device for the TFT substrate are enhanced.

The present disclosure provides an image calibrating method of a testing apparatus for a thin film transistor substrate, comprising following steps of: calculating an image offset value by using coordinate information of each pixel in a prescribed target image obtained by the testing apparatus for the thin film transistor substrate; and determining whether the offset value is smaller than a prescribed threshold value, in a case where the offset value is not smaller than the prescribed threshold value, adjusting the image by using the offset value and recalculating the offset value by using the coordinate information of each pixel in the adjusted image; in a case where the offset value is smaller than the prescribed threshold value, calibrating the image obtained by the testing apparatus for the thin film transistor substrate with the offset value as a calibrating value.

In the above solution, the step of calculating the image offset value with coordinate information of each pixel in the prescribed target image obtained by the testing apparatus for the thin film transistor substrate comprises: calculating an image offset rotation angle, an X axis offset and a Y axis offset of the image respectively as the image offset value with the coordinate information of each pixel in the obtained image and the coordinate information of the prescribed target image.

In the above solution, the step of adjusting the image with the obtained image offset value comprises: checking whether there is a historical offset value; in a case where there is a historical offset value, retrieving the historical offset value; adding the historical value with the offset value to obtain an updated historical offset value; and adjusting the offset rotation angle, X axis coordinate and Y axis coordinate of each pixel in the image with the updated historical offset value; in a case where there is no historical offset value, setting the offset value as the historical offset value, and adjusting the offset rotation angle, X axis coordinate and Y axis coordinate of each pixel in the image with the historical offset value.

In the above solution, the step of recalculating the offset value with the coordinate information of each pixel in the adjusted image comprises: calculating the image offset rotation angle, X axis offset and Y axis offset of the image respectively as the image offset value with the coordinate information of each pixel in the adjusted image and the coordinate information of the prescribed target image.

In the above solution, the prescribed target is a reflective mirror having a prescribed pattern.

The present disclosure further provides an image calibrating device of a testing apparatus for a thin film transistor substrate, the device comprising: an image processing module, a data processing module and a control module.

The image processing module is designed to transmit coordinate information of each pixel in a prescribed target image obtained by the testing apparatus for the thin film transistor substrate to the data processing module; according to a notification from the control module, the image processing module continues to obtain the prescribed target image from the testing apparatus for the thin film transistor substrate and transmits the coordinate information of each pixel in the image to the data processing module;

The data processing module is designed to calculate image offset value with the coordinate information of each pixel in the image and transmit the image offset value to the control module; the data processing module is further designed to adjust the image transmitted from the image processing module with the offset value; and the data processing module is further designed to recalculate the offset value with the coordinate information of each pixel in the adjusted image and transmit the offset value to the control module;

The control module is designed to determine whether the offset value is smaller than a prescribed threshold value: in a case where the offset value is not smaller than the prescribed threshold value, the control module notifies the image processing module to continue to obtain the prescribed target image from the testing apparatus for the thin film transistor substrate; in a case where the offset value is smaller than the prescribed threshold value, the image obtained by the testing apparatus for the thin film transistor substrate is calibrated with the offset value as a calibrating value.

In the above solution, the data processing module is designed to calculate an image offset rotation angle, X axis offset and Y axis offset of the image respectively as the image offset value with the coordinate information of each pixel in the obtained image and the coordinate information of the prescribed target image.

In the above solution, the data processing module is designed to check whether there is a historical offset value, in a case where there is a historical offset value, the historical offset value is retrieved and added with the offset value to obtain an updated historical offset value, then the offset rotation angle, X axis coordinate and Y axis coordinate of each pixel in the image are adjusted with the updated historical offset value; in a case where there is no historical offset value, the offset value is set as the historical offset value, and the offset rotation angle, X axis coordinate and Y axis coordinate of each pixel in the image are adjusted with the historical offset value.

In the above solution, the data processing module is designed to calculate the image offset rotation angle, X axis offset and Y axis offset of the image respectively as the image offset value with the coordinate information of each pixel in the adjusted image and the coordinate information of the prescribed target image.

In the above solution, the prescribed target is a prescribed reflective mirror having a prescribed pattern.

The present disclosure further provides a testing apparatus for TFT substrate, including a detecting modulator and the above image calibrating device. The prescribed target is configured at a bottom of the detecting modulator in the testing apparatus for the TFT substrate.

According to the image calibrating method and device of the testing apparatus of the present invention, an image offset value is calculated with coordinate information of each pixel in a prescribed target image obtained by the testing apparatus for the TFT substrate. Then it is determined whether the offset value is smaller than a prescribed threshold value. In a case where the offset value is not smaller than the prescribed threshold value, the image is adjusted with the offset value, and the offset value is recalculated with the coordinate information of each pixel in the adjusted image. In a case where the offset value is smaller than the prescribed threshold value, the image obtained by the testing apparatus for the TFT substrate is calibrated by using the offset value as a calibrating value. Thus, it can be determined whether the calibrating is finished by detecting whether the offset value of the prescribed target image is smaller than the prescribed threshold value. Therefore, the problem of low calibrating efficiency and accuracy of empirical manual adjustment is avoided.

DESCRIPTION OF THE EMBODIMENTS

Figure 1:
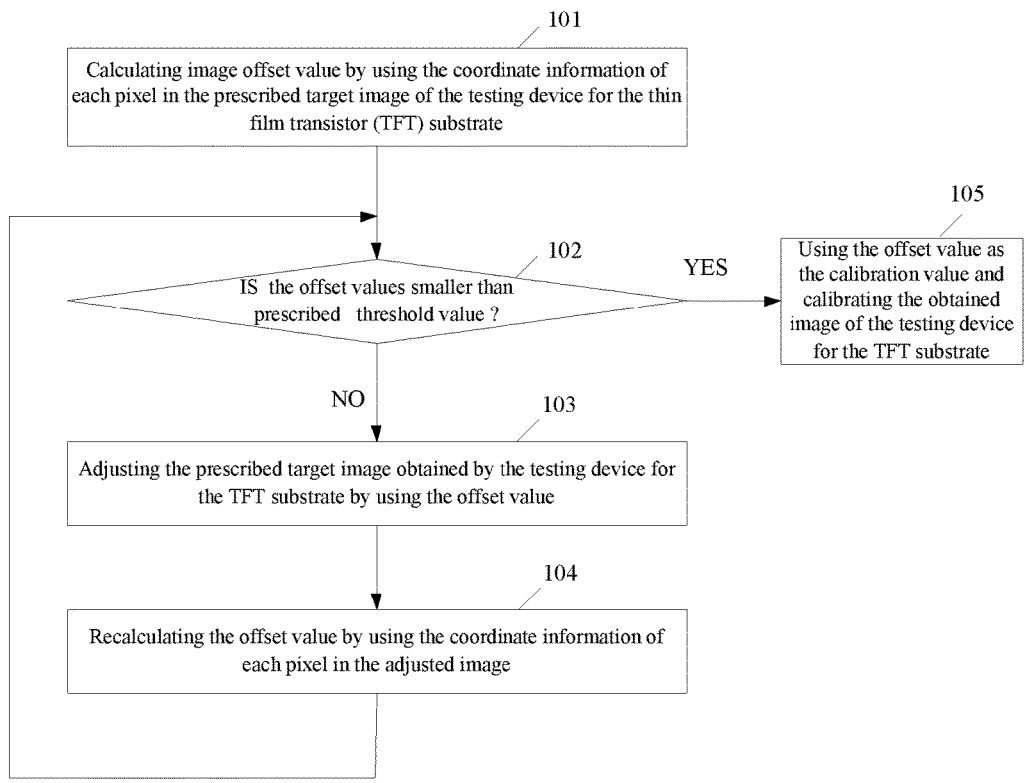
FIG. 1 is a flow chart of an image calibrating method of the testing apparatus for the TFT substrate according to an embodiment of the present disclosure.

The technical solution of the embodiments of the present disclosure will be described clearly and fully in connection with the drawings of the embodiments of the present disclosure. It is obvious that the described embodiments are just a part but not all of the embodiments of the present disclosure. Based on the described embodiments of the present disclosure, those skilled in the art can obtain all other embodiment without any inventive work, which all fall into the scope of the claimed invention.

Unless otherwise defined, technical terms or scientific terms used herein shall have a common meaning known by those skilled in the art of the present disclosure. Words and expressions such as "first", "second" and the like used in the description and claims of the patent application of the present disclosure do not denote any sequence, quantity or importance, but distinguish different components. Likewise, words such as "a", "an" and the like do not denote quantitative restrictions, but denote the presence of at least one. Words such as "connected", "connecting" and the like are not restricted to physical or mechanical connections, but may include electrical connections, regardless of direct or indirect connections. Words such as "up", "below", "left", "right", etc., are only used to denote the relative positional relationship. Upon the absolute position of the described object changes, the relative positional relationship change correspondingly.

The calibrating method of the testing apparatus for the TFT substrate known by the applicant comprises following steps. Firstly, the detecting modulator and the CCD are roughly calibrated by using a voltage image optical system (VIOS). Then, a central pixel coordinate of the motion image of the TFT substrate generated by the CCD is obtained by software, and an offset value of the central pixel coordinate of the motion image relative to a center position is estimated. Next, based on the offset value, the central pixel coordinate of the motion image of the TFT substrate generated by the CCD is adjusted. Next, it is observed whether the adjusted central pixel coordinate of the motion image is positioned at the center. In a case where the adjusted central pixel coordinate of the motion image is not positioned at the center, the offset value of a central pixel coordinate of a motion image relative to the center position is estimated continuously. Finally, based on the offset value, the central pixel coordinate of the motion image of the TFT substrate generated by the CCD is continued to be adjusted until the central pixel coordinate of the motion image is positioned at the center.

However, with the development of various kinds of TFT substrate design and the increasing design complexity and the enhancement of the image resolution, it is more and more difficult to estimate the offset according to the motion image of the TFT substrate. Thus, it relies on empirical manual adjustment. In this way, the problem of the low calibrating efficiency and low accuracy of the testing apparatus for the TFT substrate occurs.

The inventors propose an image calibrating method of a testing apparatus for a thin film transistor substrate, comprising following steps of: calculating an image offset value by using coordinate information of each pixel in a prescribed target image obtained by the testing apparatus for the thin film transistor substrate; and determining whether the offset value is smaller than a prescribed threshold value, in a case where the offset value is not smaller than the prescribed threshold value, adjusting the image by using the offset value and recalculating the offset value by using the coordinate information of each pixel in the adjusted image; in a case where the offset value is smaller than the prescribed threshold value, calibrating the image obtained by the testing apparatus for the thin film transistor substrate with the offset value as a calibrating value.

The calibrating method according to an embodiment of the present disclosure is further described as below in combination of the drawings and specific embodiment.

As illustrated in FIG. 1, the calibrating method of the testing apparatus for the TFT substrate according to the embodiment of the present disclosure comprises the following steps.

Step 101: by using coordinate information of each pixel in an image of a prescribed target obtained by the testing apparatus for the TFT substrate, an offset value of the image is calculated.

Figure 2:
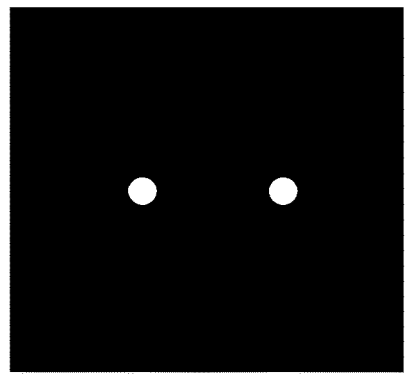
FIG. 2 is a schematic view of a prescribed target.

The prescribed target herein is for example a prescribed reflective mirror having a prescribed pattern configured at a bottom of the detecting modulator of the testing apparatus for the TFT substrate, thus the prescribed target image is the prescribed image. As illustrated in FIG. 2, the prescribed target image includes two pixels having coordinate information.

In particular, the step of calculating the image offset value with coordinate information of each pixel in the prescribed target image obtained by the testing apparatus for the thin film transistor substrate comprises: calculating an offset rotation angle, an X axis offset and a Y axis offset of the image respectively as the offset value of the image, based on the coordinate information of each pixel in the obtained image and the coordinate information of the prescribed target image.

The method of calculating the offset rotation angle is calculating the difference between the currently obtained prescribed target image rotation angle and the prescribed target image angle based on the triangle tangent formula.

Figure 3:
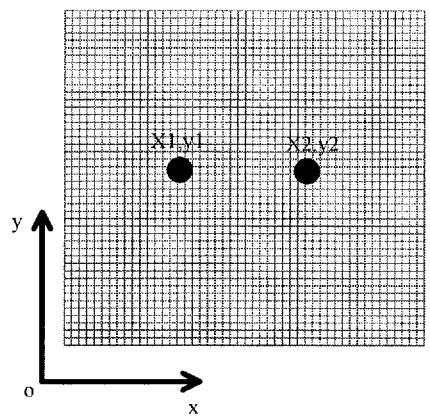
FIG. 3 is a schematic view of the prescribed target with coordinate information.
Figure 4:
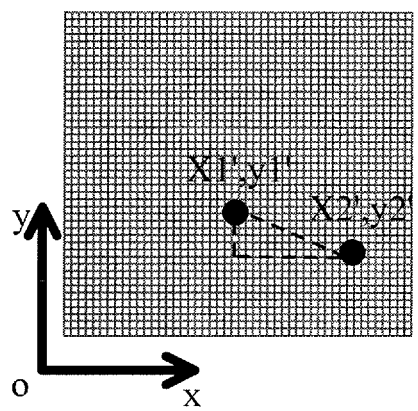
FIG. 4 is a schematic view of a collected image with the coordinate information.

For example, the prescribed target image is illustrated in FIG. 2, the coordinate information (x1, y1) and (x2, y2) of the prescribed target image is illustrated in FIG. 3, and the coordinate information (x1', y1') and (x2', y2') of the currently obtained prescribed target image of the testing apparatus for the TFT substrate is illustrated in FIG. 4. According to the triangle tangent formula, the rotation angle of the prescribed target image is calculated as $$\theta = \arctan\frac{y1 - y2}{x1 - x2}$$

and in case that the rotation angle of the currently obtained image is $$\theta' = \arctan\frac{y1' - y2'}{x1' - x2'}$$

the offset rotation angle of the image is $\Delta\theta=\theta'-\theta$; the X axis offset value is $$x = \frac{(x1' - x1) + (x2' - x2)}{2};$$

and the Y axis offset value is $$y = \frac{(y1' - y1) + (y2' - y2)}{2}$$

by calculation.

Step 102: it is determined whether the offset value is smaller than a prescribed threshold value. In a case where the offset value is smaller than the prescribed threshold value, step 105 is performed and the offset value is used as a calibrating value and the image obtained by the testing apparatus for the TFT substrate is calibrated based on the calibrating value, and the process is finished; otherwise, step 103 is performed.

The prescribed threshold value herein include: the threshold value of the rotation angle, the threshold value of the X axis offset value and the threshold value of the Y axis offset value.

Step 103: the prescribed target image obtained by the testing apparatus for the TFT substrate is adjusted by using the offset value.

For example, it is check whether there is a historical offset value. In a case where historical offset value is present, the historical offset value is retrieved and added with the offset value to obtain an updated historical offset value. The offset rotation angle, X axis coordinate and Y axis coordinate of each pixel in the image are adjusted by using the updated historical offset value. In a case where no historical offset value are present, the offset value are set as the historical offset value. The offset rotation angle, X axis coordinate and Y axis coordinate of each pixel in the image are adjusted by using the historical offset value.

Step 104: the offset value are recalculated by using the coordinate information of each pixel in the adjusted image and the process returns to step 102.

For example, the image offset rotation angle, X axis offset and Y axis offset of the image are calculated respectively as the image offset value by using the coordinate information of each pixel in the adjusted image and the coordinate information of the prescribed target image.

Figure 5:
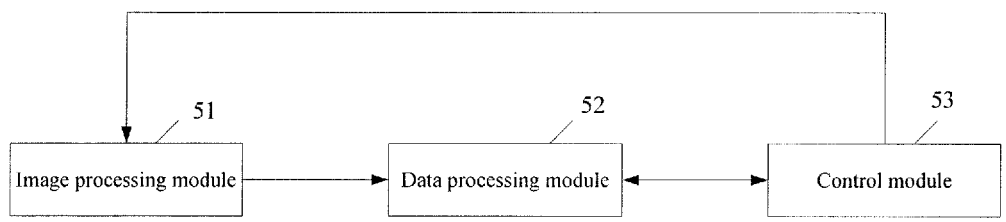
FIG. 5 is a schematic block diagram of an image calibrating device for the TFT substrate according to an embodiment of the present disclosure.

FIG. 5 is a schematic block diagram of the image calibrating device for the TFT substrate according to an embodiment of the present disclosure. As illustrated in FIG. 5, the image calibrating device includes: an image processing module 51, a data processing module 52 and a control module 53.

The image processing module 51 is designed to transmit the coordinate information of each pixel in a prescribed target image obtained by the testing apparatus for the TFT substrate to the data processing module 52. According to the notification from the control module 53, the image processing module 51 continues to obtain the prescribed target image from the testing apparatus for the TFT substrate and transmit the coordinate information of the each pixel in the image to the data processing module 52.

The data processing module 52 is designed to calculate the image offset value by using the coordinate information of each pixel in the image received form the image processing module 51, and send the offset value to the control module 53. The data processing module 52 is further designed to adjust the image transmitted from the image processing module 51 by using the offset value. The data processing module 52 is further designed to recalculate the offset value by using the coordinate information of each pixel in the adjusted image, and transmit the offset value to the control module 53.

The control module 53 is designed to determine whether the offset value is smaller than the prescribed threshold value. In a case where the offset value is not smaller than the prescribed threshold value, the control module 53 notifies the image processing module 51 to continue to obtain the prescribed target image from the testing apparatus for the TFT substrate. In a case where the offset value is smaller than the prescribed threshold value, the image obtained by the testing apparatus for the TFT substrate is calibrated by using the offset value as a calibrating value.

The data processing module 52 is designed to calculate an image offset rotation angle, X axis offset and Y axis offset of the image respectively as the image offset value by using the coordinate information of each pixel in the obtained image and coordinate information of the prescribed target image.

The data processing module 52 is designed to adjust the rotation angle, the X axis coordinate and the Y axis coordinate of each pixel in the image by using the offset value.

The data processing module 52 is designed to check whether there is a historical offset value. In a case where the historical offset value is present, the historical offset value is retrieved and added with the offset value to obtain updated historical offset value. The offset rotation angle, X axis coordinate and Y axis coordinate of each pixel in the image are adjusted by using the updated historical offset value. In a case where no historical offset value is present, the offset value is set as the historical offset value. The offset rotation angle, X axis coordinate and Y axis coordinate of each pixel in the image are adjusted by using the historical offset value.

The data processing module 52 is designed to calculate the currently obtained target image rotation angle and the prescribed target image angle by the triangle tangent formula, and set the difference between he currently obtained target image rotation angle and the prescribed target image angle as the offset rotation angle.

For example, the prescribed target image is illustrated in FIG. 2, the coordinate information (x1, y1) and (x2, y2) of the prescribed target image is illustrated in FIG. 3 and the coordinate information (x1', y1') and (x2', y2') of the obtained target image of the testing apparatus for the TFT substrate is illustrated in FIG. 4. According to the triangle tangent formula, the rotation angle of the prescribed target image is calculated as $$\theta = \arctan\frac{y1 - y2}{x1 - x2}$$

and the rotation angle of the currently obtained image is $$\theta' = \arctan\frac{y1' - y2'}{x1' - x2'}$$

and the image offset rotation angle is calculated as $\Delta\theta=\theta'-\theta$; the X axis offset value is $$x = \frac{(x1' - x1) + (x2' - x2)}{2};$$

and the Y axis offset value is $$y = \frac{(y1' - y1) + (y2' - y2)}{2}.$$

For example, the prescribed target herein is a reflective mirror having a prescribed pattern configured at the bottom of the detecting modulator of the testing apparatus for the TFT substrate.

Figure 6:
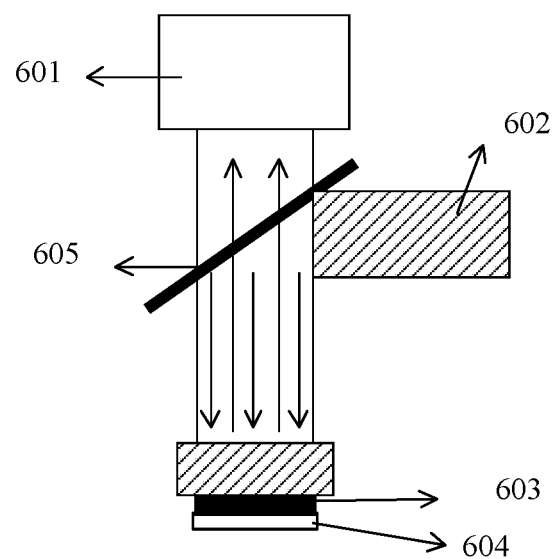
FIG. 6 is a structural schematic view of the testing apparatus for the TFT substrate.

For example, the calibrating device of the testing apparatus for the TFT substrate according to the embodiment of the present disclosure can be connected to a CCD of the testing apparatus for the TFT substrate. FIG. 6 is a structural schematic view of the testing apparatus for the TFT substrate. As illustrated in FIG. 6, the testing apparatus for the TFT substrate comprises: a CCD 601, a light source 602, a detecting modulator 603, a reflective mirror 604 configured at the bottom of the detecting modulator 603; and a lens 605. The reflective mirror 604 has a prescribed pattern so that a part of the reflective mirror fully reflects lights and other parts of the mirror do not reflect lights.

The testing apparatus for the TFT substrate collects the prescribed target image by using following procedure. Lights emitted from the light source 602 of the testing apparatus for the TFT substrate vertically incident on the detecting modulator 603 through the lens 605. The lights are reflected to the CCD 601 by the reflective mirror 604 having the prescribed pattern configured at the bottom of the detecting modulator 603. The light signals received by the CCD 601 are processed and transformed into an image.

The above embodiments are presented for illustrating the present disclosure, not intended to limit the scope of the present disclosure. Those skilled in the art can make various changes and modifications without departing from the spirit and scope of the present disclosure. Therefore, all equivalent technical solutions fall into the scope of the present disclosure. The scope that the present disclosure claims to protect is defined by the claims appended hereto.

The present application claims the priority of China Patent Application No. 2013104118622.1 filed on Sep. 13, 2013, which is incorporated herein by reference in its entirety as part of the present application.

What is claimed is:

1. An image calibrating method of a testing apparatus for a thin film transistor substrate, comprising:
    obtaining from the testing apparatus coordinate information of pixels in an image of a prescribed target including a plurality of pixels and sending the coordinate information to a data processor by an image processor;
    calculating an offset value, and sending the offset value to a controller by the data processor, wherein the offset value is calculated by comparing the coordinate information and preset coordinate information of the pixels;
    determining whether the offset value is smaller than a prescribed threshold value by the controller,
    in a case where the offset value is not smaller than the prescribed threshold value, setting the offset value as a historical offset value and adjusting the image by using the offset value by the controller, and recalculating the offset value by using the coordinate information of the pixels in the adjusted image by the data processor;
    in a case where the offset value is smaller than the prescribed threshold value, checking whether there is the historical offset value by the data processor, in a case where there is the historical offset value, retrieving the historical offset value and summing the historical value to obtain an overall offset value.

2. The method of claim 1, wherein the prescribed target is a reflective mirror having a prescribed pattern.

3. The method of claim 1, wherein the step of recalculating the offset value comprises: calculating an offset rotation angle, an X axis offset and a Y axis offset respectively as the offset value between the coordinate information of the pixels in the adjusted image and the preset coordinate information of the pixels.

4. The method of claim 3, wherein the prescribed target is a reflective mirror having a prescribed pattern.

5. The method of claim 1, wherein recalculating the offset value with the coordinate information of the pixels in the adjusted image comprises: calculating an offset rotation angle, an X axis offset and a Y axis offset respectively as the offset value between the coordinate information of the pixels in the adjusted image and the preset coordinate information of the pixels.

6. The method of claim 1, wherein calculating the offset value comprises:
    obtaining coordinate information of two pixels of the pixels from the image processor by the data processor and comparing the coordinate information and preset coordinate information of the two pixels.

7. An image calibrating device of a testing apparatus for a thin film transistor substrate, the device comprising: an image processor, a data processor, a controller and a memory for storing computer program instructions; wherein, the computer program instructions, when being executed by the image processor, perform:

obtaining from the testing apparatus coordinate information of pixels in an image of a prescribed target including a plurality of pixels and sending the coordinate information to a data processor;

the computer program instructions, when being executed by the data processor, perform:

calculating and recalculating an offset value, and sending the offset value to a controller, wherein the offset value is calculated by comparing the coordinate information and preset coordinate information of the pixels; and checking whether there is a historical offset value, in a case where there is a historical offset value, retrieving the historical offset value and summing the historical value;

the computer program instructions, when being executed by the controller, perform:

determining whether the offset value is smaller than a prescribed threshold value by the controller, in a case where the offset value is not smaller than the prescribed threshold value, adjusting the image by using the offset value and setting the offset value as the historical offset value.

8. The device of claim 7, wherein the prescribed target is a prescribed reflective mirror having a prescribed pattern.

9. The device of claim 7, wherein the computer program instructions, when being executed by the data processor, further:

calculating an offset rotation angle, X axis offset and Y axis offset respectively as the offset value with the coordinate information of the pixels in the adjusted image and the preset coordinate information of the pixels.

10. The device of claim 9, wherein the prescribed target is a prescribed reflective mirror having a prescribed pattern.

11. A testing apparatus for a TFT substrate, comprising a detecting modulator and an image calibrating device comprising: an image processor, a data processor, a controller and a memory for storing computer program instructions; wherein, the computer program instructions, when being executed by the image processor, perform:

obtaining from the testing apparatus coordinate information of pixels in an image of a prescribed target including a plurality of pixels and sending the coordinate information to a data processor;

the computer program instructions, when being executed by the data processor, perform:

calculating and recalculating an offset value, and sending the offset value to a controller, wherein the offset value is calculated by comparing the coordinate information and preset coordinate information of the pixels; and checking whether there is a historical offset value, in a case where there is a historical offset value, retrieving the historical offset value and summing the historical value;

the computer program instructions, when being executed by the controller, perform:

determining whether the offset value is smaller than a prescribed threshold value by the controller, in a case where the offset value is not smaller than the prescribed threshold value, setting the offset value as a historical offset value and adjusting the image by using the offset value;

the prescribed target is configured at a bottom of the detecting modulator.

\* \* \* \* \*